United States Patent
Liversidge et al.

(10) Patent No.: US 6,267,989 B1
(45) Date of Patent: Jul. 31, 2001

(54) METHODS FOR PREVENTING CRYSTAL GROWTH AND PARTICLE AGGREGATION IN NANOPARTICULATE COMPOSITIONS

(75) Inventors: Elaine Liversidge, West Chester; Greta A. Gottardy, Lansdale; Linden Wei, Exton, all of PA (US)

(73) Assignee: Klan Pharma International Ltd., Shannon (IE)

( * ) Notice: Subject to any disclaimer, the term of this patent is extended or adjusted under 35 U.S.C. 154(b) by 0 days.

(21) Appl. No.: 09/263,834

(22) Filed: Mar. 8, 1999

(51) Int. Cl.[7] .............................. A61K 9/14; A61K 9/16; A61K 9/50
(52) U.S. Cl. .................. 424/489; 424/493; 424/494; 424/490; 424/495; 424/499
(58) Field of Search .................... 424/489, 490, 424/495, 499, 493, 494; 514/970

(56) References Cited

U.S. PATENT DOCUMENTS

| 5,145,684 | * | 9/1992 | Liversidge et al. | 424/489 |
|---|---|---|---|---|
| 5,298,262 | | 3/1994 | Na et al. | 424/489 |
| 5,302,401 | | 4/1994 | Liversidge et al. | 424/501 |
| 5,346,702 | * | 9/1994 | Na et al. | 424/490 |
| 5,352,459 | | 10/1994 | Hollister et al. | 424/489 |
| 5,399,363 | | 3/1995 | Liversidge et al. | 424/490 |
| 5,470,583 | | 11/1995 | Na et al. | 424/489 |
| 5,662,883 | | 9/1997 | Bagchi et al. | 424/9.4 |
| 5,665,331 | | 9/1997 | Bagchi et al. | 424/9.45 |

FOREIGN PATENT DOCUMENTS

| 0 262 560 | 4/1988 | (EP) . |
|---|---|---|
| 0 499 299 | 8/1992 | (EP) . |
| 0 577 215 | 1/1994 | (EP) . |
| 0 600 532 | 6/1994 | (EP) . |

* cited by examiner

Primary Examiner—Thurman K. Page
Assistant Examiner—Blessing Fubara
(74) Attorney, Agent, or Firm—Foley & Lardner

(57) ABSTRACT

The present invention is directed to methods for preventing crystal growth and particle aggregation in nanoparticulate compositions. The methods comprise reducing a nanoparticulate composition to an optimal effective average particle size. The resultant nanoparticulate compositions exhibit prolonged particle size stability and minimal crystal growth, even following exposure to elevated temperatures.

31 Claims, 5 Drawing Sheets

5 Days Stability
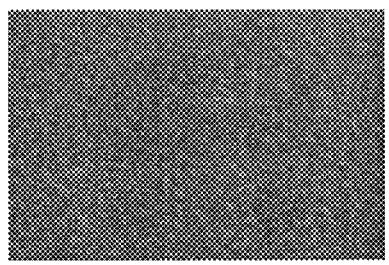
Figure 1: 5% Compound A + 2.5% HPC-SL (24 hours milling)
5 days stability in the cold
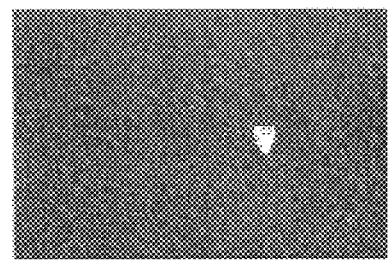
Figure 2: 5% Compound A + 2.5% HPC-SL (48 hours milling)
5 days stability in the cold
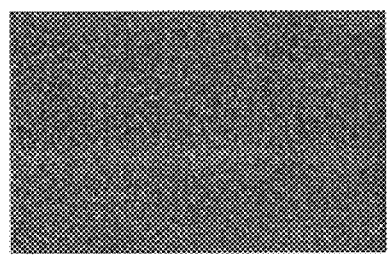
Figure 3: 5% Compound A + 2.5% HPC-SL + 0.4% PVP C-15
(24 hours milling) 5 days stability in the cold
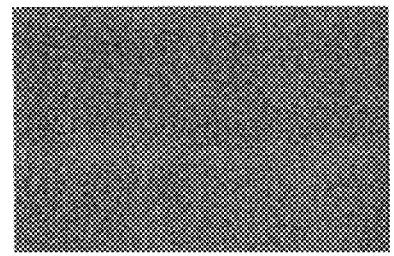
Figure 4: 5% Compound A + 2.5% HPC-SL + 0.4% PVP C-15
(48 hours milling) 5 days stability in the cold

2 Weeks Stability
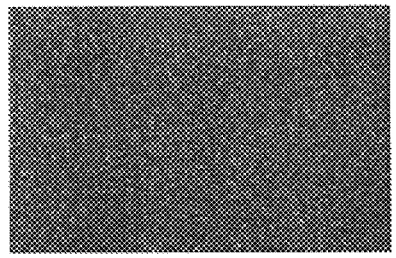
Figure 5: 5% Compound A + 2.5% HPC-SL (24 hours milling) 2 weeks stability in the cold
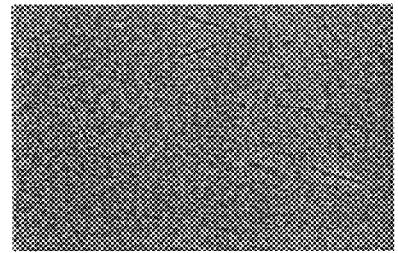
Figure 6: 5% Compound A + 2.5% HPC-SL (48 hours milling) 2 weeks stability in the cold
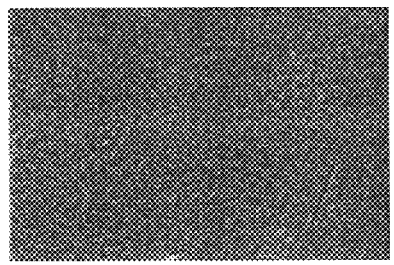
Figure 7: 5% Compound A + 2.5% HPC-SL +0.4% PVP C-15 (24 hours milling) 2 weeks stability in the cold
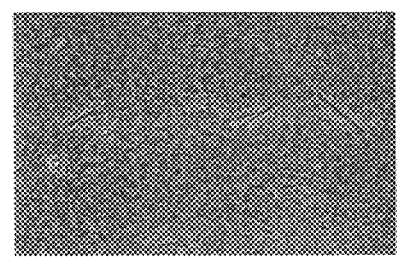
Figure 8: 5% Compound A + 2.5% HPC-SL +0.4% PVP C-15 (48 hours milling) 2 weeks stability in the cold 1 Month Stability
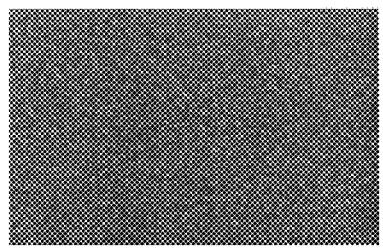
Figure 9: 5% Compound A + 2.5% HPC-SL (24 hours milling)
1 month stability in the cold
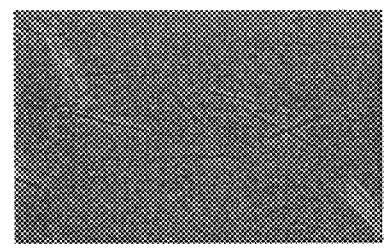
Figure 10: 5% Compound A + 2.5% HPC-SL (48 hours milling)
1 month stability in the cold
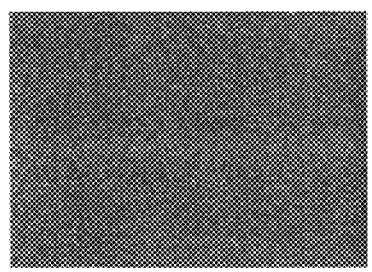
Figure 11: 5% Compound A + 2.5% HPC-SL +0.4% PVP C-15
(24 hours milling) 1 month stability in the cold
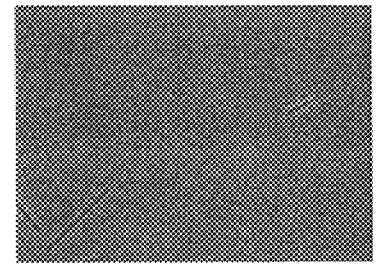
Figure 12: 5% Compound A + 2.5% HPC-SL + 0.4% PVP C-15
(48 hours milling) 1 month stability in the cold 4 Months Stability
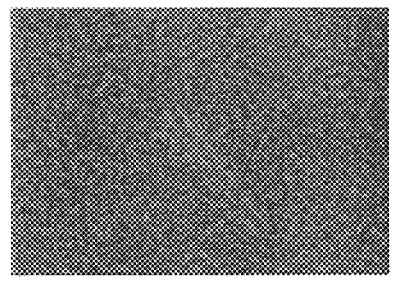 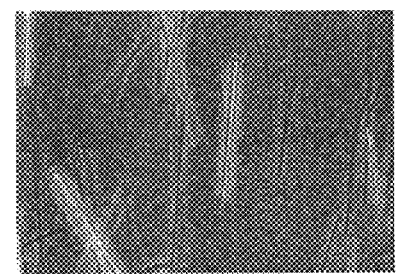
Figure 13: 5% Compound A + 2.5% HPC-SL (24 hours milling) 4 months stability in the cold
Figure 14: 5% Compound A + 2.5% HPC-SL (48 hours milling) 4 months stability in the cold 7 Months Stability
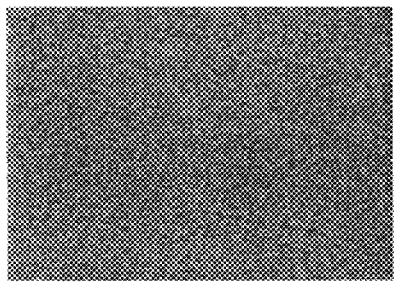 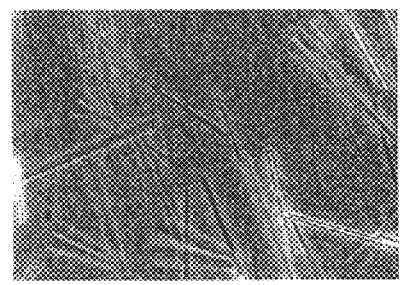
Figure 15: 5% Compound A + 2.5% HPC-SL (24 hours milling)
7 months stability in the cold
Figure 16: 5% Compound A + 2.5% HPC-SL (48 hours milling)
7 months stability in the cold

METHODS FOR PREVENTING CRYSTAL GROWTH AND PARTICLE AGGREGATION IN NANOPARTICULATE COMPOSITIONS

FIELD OF THE INVENTION

The present invention is directed to methods for preventing crystal growth and particle aggregation in nanoparticulate compositions. The methods comprise reducing a nanoparticulate composition to an optimal effective average particle size. The resultant nanoparticulate compositions exhibit particle size stability and minimal crystal growth, even following prolonged storage periods and/or exposure to elevated temperatures.

BACKGROUND OF THE INVENTION

Nanoparticulate compositions, which were first described in U.S. Pat. No. 5,145,684 ("the '684 Patent"), comprise a poorly soluble crystalline drug and a non-crosslinked surface stabilizer adsorbed to the surface of the drug. Nanoparticulate compositions are superior to macro-sized particulate drug formulations, as nanoparticulate drug formulations can exhibit reduced toxicity and enhanced efficacy (U.S. Pat. No. 5,399,363), enhanced bioavailability (U.S. Pat. No. 5,662,883), and enhanced stability (U.S. Pat. No. 5,665,331).

However, one of the problems that may be encountered with some nanoparticulate compositions is the solubilization and subsequent recrystallization of the component crystalline drug particles. This process results in large crystal formation over a period of time in the nanoparticulate composition. In addition, some nanoparticulate formulations exhibit particle aggregation over a period of time. Although such crystal growth and particle aggregation are often insignificant under normal conditions, under certain circumstances substantial crystal growth and particle aggregation can occur. This is observed with particular combinations of drugs and surface stabilizers, and even more so when the nanoparticulate composition is exposed to elevated temperatures for heat sterilization.

Crystal growth and particle aggregation in nanoparticulate preparations are highly undesirable for several reasons. Crystals in the nanoparticulate composition may cause increased toxic effects of the active ingredient, especially when the preparation is in an injectable formulation. This is also true for particle aggregation, as injectable formulations preferably have an effective average particle size of no greater than 250 nm.

In addition, for oral formulations, the presence of crystals and/or particle aggregation, and therefore varying particle sizes, creates a variable bioavailability profile because smaller particles dissolve faster than the larger aggregates or larger crystal particles. For drugs whose bioavailabiliy is dissolution-rate limited, a faster rate of dissolution is associated with greater bioavailability, and a slower rate of dissolution is associated with a lower bioavailability. This is because bioavailability is proportional to the surface area of an administered drug and, therefore, bioavailability increases with a reduction in the particle size of the dispersed agent (see U.S. Pat. No. 5,662,833). With a composition having widely varying particle sizes, bioavailability becomes highly variable and inconsistent and dosage determinations become difficult. Moreover, because such crystal growth and particle aggregation are uncontrollable and unpredictable, the quality of the nanoparticulate compositions is inconsistent. Finally, the mere occurrence of crystal growth indicates that the nanoparticulate formulation is not a "stable" pharmaceutical formulation, because such crystal growth indicates that the nanoparticulate drug particles are continually solubilizing and recrystallizing. This may in turn cause degradation of the active ingredient with numerous undesirable ramifications.

Two accepted methods (there are others, e.g. gamma irradiation) for sterilizing pharmaceutical products are heat sterilization and sterile filtration. Sterile filtration is an effective method for sterilizing solutions having a particle size of less than 0.22 microns (220 nm), because a 0.22 micron mesh size filter is sufficient to remove most bacteria. However, because nanoparticulate compositions have a size range, many of the particles of a typical nanoparticulate composition having an effective average particle size of 220 nm may have a size greater than 220 nm. and/or due to their shape, cannot be effectively sterilized by conventional filters. Such larger rigid crystal particles tend to clog the sterile filter. Thus, only nanoparticulate compositions having very small effective average particle sizes can be sterile filtered.

Sterile filtration is less desirable than conventional autoclaving (steam heat) at 121° C. This is because with heat sterilization, the nanoparticulate composition is placed in the final storage container and sterilized (a single-step process). The product can then be marketed in the heat sterilized container. In contrast, the filter-sterilization step of sterile filtration is followed by a packaging step (a two-step process). The secondary packaging step of sterile filtration substantially increases the risk of contamination as compared to conventional autoclaving. For these reasons, the Food and Drug Administration generally requires submission of data demonstrating that a formulation cannot be autoclaved before approval of sterile filtration as a method of sterilization for a sterile product.

While crystal growth and particle aggregation in nanoparticulate compositions can occur over extended storage periods, such phenomena are more often observed after heat sterilization of the compositions. Aggregation of nanoparticle compositions upon heating is directly related to the precipitation of the surface stabilizer at temperatures above the cloud point of the surface stabilizer. At this point, the bound surface stabilizer molecules are likely to dissociate from the nanoparticles and precipitate, leaving the nanoparticles unprotected. The unprotected nanoparticles then aggregate into clusters of particles. Upon cooling, the surface stabilizer re-dissolves into the solution, which then coats the aggregated particles and prevents them from dissociating into smaller particles.

Several methods have been suggested in the prior art for preventing crystal growth and particle aggregation following heat sterilization, including adding a cloud point modifier or crystal growth modifier to the nanoparticulate composition and purifying the surface stabilizer. For example, U.S. Pat. No. 5,298,262 describes the use of an anionic or cationic cloud point modifier in nanoparticulate compositions and U.S. Pat. No. 5,346,702 describes nanoparticulate compositions having a nonionic surface stabilizer and a non-ionic cloud point modifier. The cloud point modifier enables heat sterilization of the nanoparticulate compositions with low resultant particle aggregation. U.S. Pat. No. 5,470,583 describes nanoparticulate compositions having a non-ionic surface stabilizer and a charged phospholipid as a cloud point modifier.

The prior art also describes methods of limiting crystal growth in a nanoparticulate composition by adding a crystal growth modifier (see U.S. Pat. Nos. 5,662,883 and 5,665,331). In addition, U.S. Pat. No. 5,302,401 describes nanoparticulate compositions having polyvinylpyrrolidone (PVP) as a surface stabilizer and sucrose as a cryoprotectant (allowing the nanoparticles to be lyophilized). The compositions exhibit minimal particle aggregation following lyophilization.

All of these various prior art methods share one common feature: they require an additional substance added to the nanoparticulate formulation to inhibit or prevent crystal growth and particle aggregation of the nanoparticulate composition. The addition of such a substance can be detrimental as it may induce adverse effects, particularly for injectable formulations. Moreover, cloud point and crystal growth modifiers are often highly toxic. Thus, this minimizes the usefulness of such substances in pharmaceutical compositions. In addition, the requirement of an additional substance to obtain a stable composition increases production costs.

Another method of limiting particle aggregation or crystal growth of nanoparticulate compositions during sterilization known prior to the present invention was the use of purified surface stabilizers. U.S. Pat. No. 5,352,459 describes nanoparticulate compositions having a purified surface stabilizer (having less than 15% impurities) and a cloud point modifier. Purification of surface stabilizers can be expensive and time consuming, thus significantly raising production costs of compositions requiring such stabilizers to produce a stable nanoparticulate composition.

There is a need in the art for nanoparticulate compositions of poorly soluble drugs that exhibit minimal particle aggregation and crystal growth, even following prolonged storage periods and/or exposure to elevated temperatures, and methods of making such compositions. The present invention satisfies these needs.

SUMMARY OF THE INVENTION

The present invention is directed to the surprising discovery that nanoparticulate compositions having an optimal effective average particle size exhibit minimal particle aggregation and crystal growth, even following prolonged storage periods or exposure to elevated temperatures.

One aspect of the invention is directed to nanoparticulate compositions comprising a poorly soluble crystalline or amorphous drug and one or more non-crosslinked surface stabilizers adsorbed to the surface of the drug, having an optimal effective average particle size of from about 150 nm to about 350 nm, more preferably from about 150 nm to about 300 nm, even more preferably from about 150 nm to about 250 nm, and most preferably from about 150 to about 200 nm. The compositions exhibit minimal particle aggregation and crystal growth following prolonged storage periods and/or exposure to elevated temperatures.

Another aspect of the invention is directed to methods of making nanoparticulate compositions exhibiting minimal particle aggregation and crystal growth over extended storage periods and/or following heat sterilization. The method comprises reducing the effective average particle size of the nanoparticulate composition to an optimal effective average particle size of from about 150 nm to about 350 nm, more preferably from about 150 nm to about 300 nm, even more preferably from about 150 nm to about 250 nm, and most preferably from about 150 to about 200 nm. Such a composition exhibits minimal particle aggregation and crystal growth following prolonged storage periods and/or following heat sterilization.

The present invention is further directed to pharmaceutical compositions comprising a nanoparticulate composition of the invention. The pharmaceutical compositions preferably comprise a pharmaceutically acceptable carrier as well as any desired excipients.

Yet another aspect of the invention encompasses a method of treating a mammal in need comprising administering a therapeutically effective amount of a nanoparticulate composition according to the invention.

Both the foregoing general description and the following detailed description are exemplary and explanatory and are intended to provide further explanation of the invention as claimed. Other objects, advantages, and novel features will be readily apparent to those skilled in the art from the following detailed description of the invention.

BRIEF DESCRIPTION OF THE FIGURES

FIG. 1: Shows a photomicrograph of a nanoparticulate composition produced after 24 hours of milling of 5% Compound A and 2.5% HPC-SL after 5 days stability in the cold;

FIG. 2: Shows a photomicrograph of a nanoparticulate composition produced after 48 hours of milling of 5% Compound A and 2.5% HPC-SL after 5 days stability in the cold;

FIG. 3: Shows a photomicrograph of a nanoparticulate composition produced after 24 hours of milling of 5% Compound A, 2.5% HPC-SL, and 0.4% polyvinylpyrrolidone (PVP) after 5 days stability in the cold;

FIG. 4: Shows a photomicrograph of a nanoparticulate composition produced after 48 hours of milling of 5% Compound A, 2.5% HPC-SL, and 0.4% after 5 days stability in the cold;

FIG. 5: Shows a photomicrograph of a nanoparticulate composition produced after 24 hours of milling of 5% Compound A and 2.5% HPC-SL after 2 weeks stability in the cold;

FIG. 6: Shows a photomicrograph of a nanoparticulate composition produced after 48 hours of milling of 5% Compound A and 2.5% HPC-SL after 2 weeks stability in the cold;

FIG. 7: Shows a photomicrograph of a nanoparticulate composition produced after 24 hours of milling of 5% L-807,067, 2.5% HPC-SL, and 0.4% PVP after 2 weeks stability in the cold;

FIG. 8: Shows a photomicrograph of a nanoparticulate composition produced after 48 hours of milling of 5% Compound A, 2.5% HPC-SL, and 0.4% PVP after 2 weeks stability in the cold;

FIG. 9: Shows a photomicrograph of a nanoparticulate composition produced after 24 hours of milling of 5% Compound A and 2.5% HPC-SL after 1 month stability in the cold;

FIG. 10: Shows a photomicrograph of a nanoparticulate composition produced after 48 hours of milling of 5% Compound A and 2.5% HPC-SL after 1 month stability in the cold;

FIG. 11: Shows a photomicrograph of a nanoparticulate composition produced after 24 hours of milling of 5% Compound A, 2.5% HPC-SL, and 0.4% PVP after 1 month stability in the cold;

FIG. 12: Shows a photomicrograph of a nanoparticulate composition produced after 48 hours of milling of 5% Compound A, 2.5% HPC-SL, and 0.4% PVP after 1 month stability in the cold;

FIG. 13: Shows a photomicrograph of a nanoparticulate composition produced after 24 hours of milling of 5% Compound A and 2.5% HPC-SL after 4 months stability in the cold; and FIG. 14: Shows a photomicrograph of a nanoparticulate composition produced after 48 hours of milling of 5% Compound A and 2.5% HPC-SL after 4 months stability in the cold.

FIG. 15: Shows a photomicrograph of a nanoparticulate composition produced after 24 hours of milling of 5% Compound A and 2.5% HPC-SL after 7 months stability in the cold.

FIG. 16: Shows a photomicrograph of a nanoparticulate composition produced after 48 hours of milling of 5% Compound A and 2.5% HPC-SL after 7 months stability in the cold.

DETAILED DESCRIPTION OF THE INVENTION

The present invention is directed to the surprising discovery that nanoparticulate compositions having an optimal particle size exhibit minimal particle aggregation and crystal growth following extended storage periods and/or following exposure to elevated temperatures.

It was known prior to the present invention that crystal growth and particle aggregation occur in some nanoparticulate compositions after extended storage periods, and that this phenomena is more prevalent in nanoparticulate compositions exposed to elevated temperatures. It was surprisingly discovered that the rate of such particle aggregation and crystal growth is dependent upon the starting particle size of the nanoparticulate dispersion. Compositions having very small nanoparticulate sizes, i.e., less than about 100 nm, and compositions having relatively large particle sizes, i.e., greater than about 400 nm, show more rapid rates of crystal growth and particle aggregation as compared to nanoparticulate compositions milled to an optimal effective average particle size, i.e., from about 150 nm to about 350 nm.

While applicants do not wish to be bound by any theory, one possibility for this observed phenomena is that nanoparticulate compositions milled to a very small effective average particle size, i.e., less than about 150 nm, have a more prevalent Ostwald ripening. Ostwald ripening occurs when small crystals, which are more soluble than larger crystals, dissolve, then recrystallize to form large crystals and particle aggregates. This may explain why nanoparticulate compositions milled to a very small particle size show significant crystal growth and particle aggregation following prolonged storage periods or exposure to elevated temperatures.

Nanoparticulate compositions having larger effective average particle sizes, i.e., larger than about 400 nm, can also show significant crystal growth and particle aggregation following prolonged storage periods. It was also surprisingly discovered that when a nanoparticulate composition has an effective average particle size of greater than about 400 nm, the resultant particle size distribution following heat sterilization is much broader than when a nanoparticulate composition having an optimal effective average particle size is heat sterilized. A wide particle size distribution is undesirable because such a composition has an inconsistent bioavailability profile, which can make dosage formulations difficult.

A. Stability of Nanoparticulate Compositions Exposed to Elevated Temperatures Prior to the present invention, sterilization of nanoparticulate compositions by conventional autoclaving at 121° C. was often ineffective because exposure to heat can stimulate crystal growth and particle aggregation. Such crystal growth and particle aggregation results in a substantial increase in the effective average particle size of the nanoparticulate composition, thus diminishing the bioavailability, decreased toxicity, and increased efficacy benefits of the nanoparticulate composition.

As described in the examples below, three nanoparticulate composition size ranges were tested: about 100 nm, about 200 nm, and about 400–500 nm. The nanoparticulate dispersion having a smaller effective average particle size, i.e., about 100 nm, showed significant particle aggregation and crystal growth following heat sterilization. When the starting particle size was about 400–500 nm, the final effective average particle size following heat sterilization of a significant number of the particles was about 700 nm or more. This particle size exceeds the preferred particle size for injectable formulations. Moreover, the nanoparticulate compositions having an effective average particle size of about 100 nm and about 400–500 nm showed a wide particle size distribution following heat sterilization. In contrast, heat sterilization of a nanoparticulate composition having an optimal effective average particle size resulted in a composition having an acceptable and narrow particle size distribution that is safe for injectable formulations.

B. Stability of Nanoparticulate Compositions after Prolonged Storage Periods Similarly, it was surprisingly discovered that particle aggregation and crystal formation in nanoparticulate compositions during storage can be prevented or minimized by reducing the nanoparticulate composition to an optimal effective average particle size of from about 150 nm to about 350 nm, more preferably from about 150 nm to about 300 nm, even more preferably from about 150 nm to about 250 nm, and most preferably from about 150 to about 200 nm.

As described in the examples below, milling to an optimal particle size of greater than 150 nm resulted in minimal or no particle aggregation or crystal growth for at least up to 7 months. The maximum storage period for sterile products is about two years.

C. Nanoparticulate Compositions

The compositions of the invention comprise nanoparticulate drug and one or more surface stabilizers adsorbed to the surface of the drug. Surface stabilizers useful herein physically adhere to the surface of the nanoparticulate drug, but do not chemically react with the drug or itself. Individually adsorbed molecules of the surface stabilizer are essentially free of intermolecular crosslinkages.

The present invention also includes nanoparticulate compositions having one or more surface stabilizers adsorbed on the surface thereof, formulated into compositions together with one or more non-toxic physiologically acceptable carriers, adjuvants, or vehicles, collectively referred to as carriers, for parenteral injection, for oral administration in solid or liquid form, for rectal or topical administration, or the like.

1. Drug Particles

The nanoparticles of the invention comprise a therapeutic or diagnostic agent, collectively referred to as a "drug." A therapeutic agent can be a pharmaceutical, including biologics such as proteins and peptides, and a diagnostic agent is typically a contrast agent, such as an x-ray contrast agent, or any other type of diagnostic material. The drug exists as a discrete, crystalline phase or as an amorphous phase. The crystalline phase differs from a non-crystalline or amorphous phase which results from precipitation techniques, such as those described in EP Patent No. 275,796.

The invention can be practiced with a wide variety of drugs. The drug is preferably present in an essentially pure form, is poorly soluble, and is dispersible in at least one liquid medium. By "poorly soluble" it is meant that the drug has a solubility in the liquid dispersion medium of less than about 10 mg/mL, and preferably of less than about 1 mg/mL.

The drug can be selected from a variety of known classes of drugs, including, for example, proteins, peptides, corticosteroids, elastase inhibitors, analgesics, anti-fungals, oncology therapies, anti-emetics, analgesics, cardiovascular agents, anti-inflammatory agents, anthelmintics, anti-arrhythmic agents, antibiotics (including penicillins), anticoagulants, antidepressants, antidiabetic agents, antiepileptics, antihistamines, antihypertensive agents, anti-muscarinic agents, antimycobacterial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (antiparkinsonian agents), haemostatics, immuriological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators and xanthines.

A description of these classes of drugs and a listing of species within each class can be found in Martindale, *The Extra Pharmacopoeia*, Twenty-ninth Edition (The Pharmaceutical Press, London, 1989), specifically incorporated by reference. The drugs are commercially available and/or can be prepared by techniques known in the art.

2. Surface stabilizers

Useful surface stabilizers include various polymers, low molecular weight oligomers, natural products, and surfactants. Preferred surface stabilizers include nonionic and ionic surfactants. Two or more surface auxiliary stabilizers can be used in combination. Representative examples of surface stabilizers include cetyl pyridinium chloride, gelatin, casein, lecithin (phosphatides), dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., Tween 20® and Tween 80® (ICI Specialty Chemicals)); polyethylene glycols (e.g., Carbowaxs 3350 ® and 1450®, and Carbopol 934® (Union Carbide)), dodecyl trimethyl ammonium bromide, polyoxyethylene stearates, colloidal silicon dioxide, phosphates, sodium dodecylsulfate, carboxymethylcellulose ti calcium, hydroxypropyl celluloses (e.g., HPC, HPC-SL, and HPC-L), hydroxypropyl methylcellulose (HPMC), carboxymethylcellulose sodium, methylcellulose, hydroxyethylcellulose, hydroxypropylcellulose, hydroxypropylmethyl-cellulose phthalate, noncrystalline cellulose, magnesium aluminum silicate, triethanolamine, polyvinyl alcohol (PVA), polyvinylpyrrolidone (PVP), 4-(1, 1,3,3-tetramethylbutyl)-phenol polymer with ethylene oxide and formaldehyde (also known as tyloxapol, superione, and triton), poloxamers (e.g., Pluronics F68® and F108®, which are block copolymers of ethylene oxide and propylene oxide); poloxamines (e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.)); a charged phospholipid such as dimyristoyl phophatidyl glycerol, dioctylsulfosuccinate (DOSS); Tetronic 1508® (T-1508) (BASF Wyandotte Corporation), dialkylesters of sodium sulfosuccinic acid (e.g., Aerosol OT®, which is a dioctyl ester of sodium sulfosuccinic acid (American Cyanamid)); Duponol P®, which is a sodium lauryl sulfate (DuPont); Tritons X-200®, which is an alkyl aryl polyether sulfonate (Rohm and Haas); Crodestas F-110®, which is a mixture of sucrose stearate and sucrose distearate (Croda Inc.); p-isononylphenoxypoly-(glycidol), also known as Olin-10G® or Surfactant 10-G® (Olin Chemicals, Stamford, Conn.); Crodestas SL-40® (Croda, Inc.); and SA9OHCO, which is $C_{18}H_{37}CH_2(CON(CH_3)-CH_2(CHOH)_4(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; and the like.

Most of these surface stabilizers are known pharmaceutical excipients and are described in detail in the *Handbook of Pharmaceutical Excipients*, published jointly by the American Pharmaceutical Association and The Pharmaceutical Society of Great Britain (The Pharmaceutical Press, 1986), specifically incorporated by reference. The surface stabilizers are commercially available and/or can be prepared by techniques known in the art.

3. Nanoparticulate Drug/Surface Stabilizer Particle Size

The compositions of the invention contain nanoparticles which have an effective average particle size of from about 150 nm to about 350 nm, more preferably from about 150 nm to about 300 nm, even more preferably from about 150 nm to about 250 nm, and most preferably from about 150 to about 200 nm, as measured by light-scattering methods. By "an effective average particle size of from about 150 nm to about 350 nm" it is meant that at least 50% of the drug particles have a weight average particle size of from about 150 nm to about 350 nm when measured by light scattering techniques. Preferably, at least 70% of the drug particles have an average particle size of from about 150 nm to about 350 nm, more preferably at least 90% of the drug particles have an average particle size of from about 150 nm to about 350 nm, and even more preferably at least about 95% of the particles have a weight average particle size of from about 150 nm to about 350 nm.

4. Concentration of Nanoparticulate Drug and Stabilizer

The relative amount of drug and one or more surface stabilizers can vary widely. The optimal amount of the one or more surface stabilizers can depend, for example, upon the particular active agent selected, the hydrophilic lipophilic balance (HLB), melting point, and water solubility of the surface stabilizer, and the surface tension of water solutions of the surface stabilizer, etc.

It was surprisingly discovered that using a smaller amount of a surface stabilizer having a lower percent solubility does not decrease crystal growth or particle aggregation, as would be expected. This is most likely because a decrease in the quantity of surface stabilizer results in greater milling efficiency and, therefore, a resultant smaller particle size. Such a resultant smaller particle size fuels crystal growth and particle aggregation.

The concentration of the one or more surface stabilizers can vary from about 0.1 to about 90%, and preferably is from about 1 to about 75%, more preferably from about 10 to about 60%, and most preferably from about 10 to about 30% by weight based on the total combined weight of the drug substance and surface stabilizer.

The concentration of the drug can vary from about 99.9% to about 10%, and preferably is from about 99% to about 25%, more preferably from about 90% to about 40%, and most preferably from about 90% to about 70% by weight based on the total combined weight of the drug substance and surface stabilizer.

D. Methods of Making Nanoparticulate Formulations

The nanoparticulate drug compositions can be made by, for example, milling or precipitation. Exemplary methods of making nanoparticulate compositions are described in the '684 patent. The optimal effective average particle size of the invention can be obtained by controlling the process of particle size reduction, such as controlling the milling time and the amount of surface stabilizer added. Crystal growth and particle aggregation can also be minimized by milling or precipitating the composition under colder temperatures, and by storing the final composition at colder temperatures.

1. Aqueous Milling to obtain Nanoparticulate Drug Dispersions

Milling of aqueous drug to obtain a nanoparticulate dispersion comprises dispersing drug particles in a liquid dispersion medium, followed by applying mechanical means in the presence of grinding media to reduce the particle size of the drug to the desired effective average particle size of from about 150 nm to about 350 nm, more preferably from about 150 nm to about 300 nm, even more preferably from about 150 nm to about 250 nm, and most preferably from about 150 to about 200 nm. The particles can be reduced in size in the presence of one or more surface stabilizers. Alternatively, the particles can be contacted with one or more surface stabilizers after attrition. Other compounds, such as a diluent, can be added to the drug/surface stabilizer composition during the size reduction process. Dispersions can be manufactured continuously or in a batch mode. The resultant nanoparticulate drug dispersion can be utilized in solid or liquid dosage formulations.

Exemplary useful mills include low energy mills, such as a roller or ball mill, and high energy mills, such as Dyno mills, Netzsch mills, DC mills, and Planetary mills.

2. Precipitation to Obtain Nanoparticulate Drug Compositions

Another method of forming the desired nanoparticle dispersion is by microprecipitation. This is a method of preparing stable dispersions of drugs in the presence of one or more surface stabilizers and one or more colloid stability enhancing surface active agents free of any trace toxic solvents or solubilized heavy metal impurities. Such a method comprises, for example: (1) dissolving the drug in a suitable solvent; (2) adding the formulation from step (1) to a solution comprising at least one surface stabilizer to form a clear solution; and (3) precipitating the formulation from step (2) using an appropriate non-solvent. The method can be followed by removal of any formed salt, if present, by dialysis or diafiltration and concentration of the dispersion by conventional means. The resultant nanoparticulate drug dispersion can be utilized in solid or liquid dosage formulations.

E. Methods of Using Nanoparticulate Drug Formulations

The nanoparticulate compositions of the present invention can be administered to humans and animals either orally, rectally, parenterally (intravenous, intramuscular, or subcutaneous), intracisternally, intravaginally, intraperitoneally, locally (powders, ointments or drops), or as a buccal or nasal spray.

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents, or vehicles include water, ethanol, polyols (propyleneglycol, polyethyleneglycol, glycerol, and the like), suitable mixtures thereof, vegetable oils (such as olive oil) and injectable organic esters such as ethyl oleate.

Proper fluidity can be maintained, for example, by the use of a coating such as lecithin, by the maintenance of the required particle size in the case of dispersions and by the use of surfactants. The nanoparticulate compositions may also contain adjuvants such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

Solid dosage forms for oral administration include capsules, tablets, pills, powders, and granules. In such solid dosage forms, the active compound is admixed with at least one of the following: (a) one or more inert excipients (or carrier), such as sodium citrate or dicalcium phosphate; (b) fillers or extenders, such as starches, lactose, sucrose, glucose, mannitol, and silicic acid; (c) binders, such as carboxymethylcellulose, alignates, gelatin, polyvinylpyrrolidone, sucrose and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as cetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, or mixtures thereof. For capsules, tablets, and pills, the dosage forms may also comprise buffering agents.

Liquid dosage forms for oral administration include pharmaceutically acceptable emulsions, solutions, suspensions, syrups, and elixirs. In addition to the active compounds, the liquid dosage forms may comprise inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, oils, such as cottonseed oil, groundnut oil, corn germ oil, olive oil, castor oil, and sesame oil, glycerol, tetrahydrofurfuryl alcohol, polyethyleneglycols, fatty acid esters of sorbitan, or mixtures of these substances, and the like.

Actual dosage levels of active ingredients in the nanoparticulate compositions of the invention may be varied to obtain an amount of active ingredient that is effective to obtain a desired therapeutic response for a particular composition and method of administration. The selected dosage level therefore depends upon the desired therapeutic effect, the route of administration, the potency of the administered drug, the desired duration of treatment, and other factors.

The total daily dose of the compounds of this invention administered to a host in single or divided dose may be in amounts of, for example, from about 1 nanomol to about 5 micromoles per kilogram of body weight. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, potency of the administered drug, rates of absorption and excretion, combination with other drugs and the severity of the particular disease being treated.

The following examples are given to illustrate the present invention. It should be understood, however, that the invention is not to be limited to the specific conditions or details described in these examples. Throughout the specification, any and all references to a publicly available document, including U.S. patents, are specifically incorporated into this patent application by reference.

EXAMPLE 1

The purpose of this example was to compare the particle size of two nanoparticulate compositions having starting particle sizes of about 190 nm and about 125 nm following various storage periods.

Two different nanoparticulate dispersions of Compound A (a compound intended to be used in the treatment of central nervous system (CNS) anxiety disorders) were prepared by roller milling. The first, a mixture of 5% Compound A and 2.5% HPC-SL (a surface stabilizer) (Nisso Chemicals), was milled for 24 hours in a 15 ml bottle filled with 7.5 ml of 0.8 mm YTZ Zirconia media (Tosoh Corp.) on a U.S. Stoneware roller mill. The final effective average particle size of this dispersion was 188 nm (Formulation A). The second nanoparticulate dispersion, a mixture of 5% Compound A, 2.5% HPC-SL, and 0.4% PVP C-15 (a crystal growth modifier) (ISP Fine Chemicals) was also milled for 24 hours in a 15 ml bottle on the same U.S. Stoneware roller mill. The final size of this dispersion was 185 nm (Formulation B).

A small sample of each dispersion was removed from the bottle and placed on stability at 2–8° C. The bottles containing the two different dispersions were then placed back on the roller mill to mill for an additional 24 hours. After a total of 48 hours of roller milling, the final particle size of the two different nanoparticulate dispersions of Compound A was determined. The first, a mixture of 5% Compound A and 2.5% HPC-SL, was milled to a particle size of 125 nm (Formulation C). The second nanoparticulate dispersion, a mixture of 5% Compound A, 2.5% HPC-SL, and 0.4% PVP C-15, was milled to a particle size of 126 nm (Formulation D). A summary of the particle size and composition of the four formulations is provided in Table 1.

TABLE 1

| Formulation | Composition | Mean Particle Size |
|---|---|---|
| A | 5% Compound A and 2.5% HPC-SL | 188 nm |
| B | 5% Compound A, 2.5% HPC-SL, and 0.4% PVP | 185 nm |
| C | 5% Compound A and 2.5% HPC-SL | 125 nm |
| D | 5% Compound A, 2.5% HPC-SL, and 0.4% PVP | 126 nm |

The stability of Formulations A, B, C, and D at 2–8° C. was monitored over time. Photomicrographs of Formulations A and B, milled to a particle size of 188 and 185 nm, were taken at 5 days, 2 weeks, and 1 month. In addition, photomicrographs were taken of Formulation A at 4 and 7 months. The Photomicrographs at 5 days stability (FIGS. 1 and 3), 2 weeks stability (FIGS. 5 and 7), and at 1 month (FIGS. 9 and 11) show no or minimal crystal growth or particle aggregation. In addition, photomicrographs of Formulation A after 4 and 7 months (FIGS. 13 and 15, respectively), show no or minimal crystal growth or particle aggregation.

In contrast, Formulations C and D, milled to a particle size of 125 and 126 nm, showed dramatic crystal growth (formation of large needle-like particles) and particle aggregation. After 5 days stability, faint crystal growth is apparent in Formulation C (FIG. 2). After 2 weeks stability, dramatic crystal growth is observed in both Formulations C and D (FIGS. 6 and 7, respectively). This trend continues, with even more dramatic crystal growth observed after 1 month stability for both Formulations C and D (FIGS. 10 and 12, respectively). Finally, Formulation C after 4 or 7 months stability is virtually useless as a pharmaceutical composition because of extensive crystal growth (FIGS. 14 and 16).

These observations were particularly surprising for Fonnulations B and D, as these formulations comprised PVP C-15, which is a crystal growth modifier. Even with the addition of a crystal growth modifier, Formulation D showed extensive crystal growth after only 2 weeks of stability.

EXAMPLE 2

The purpose of this example was to determine the effect of the starting particle size of a nanoparticulate composition on the final particle size of the composition following heat sterilization.

Three nanoparticulate formulations of Compound B (an immunesuppressant or antibiotic with immunesuppressant capability) and as a surface stabilizer Pluronic F68™ (a block copolymer of ethylene oxide and propylene oxide; BASF Wyandotte Corporation, Parsippany, N.J.)) were made. The three formulations had different particle size ranges: (1) Formulation S, having a mean particle size of about 110 nm; (2) Formulation M, having a mean particle size of 155 to 220 nm; and (3) Formulation L, having a mean particle size of about 300 nm.

Formulation S was prepared in a two step milling process. For the first step, a slurry was prepared, containing 20 grams of Compound B and 10 grams of Pluronic F68 in 55 grams of water for injection. 85 grams of the slurry and 130 ml of 500 $\mu$m polymeric media were loaded in a 150 ml chamber and milled in a circulation mode in a Dyno mill (Glen Mills, Inc., Clifton, N.J.) for 3½ hours. For the second milling step, 85 grams of diluted dispersion from the first step was milled in a batch mode, with 50 $\mu$m polymeric media in a 150 ml chamber, for 1½ hours.

For Formulations M and L, a roller milling process was used. A slurry was prepared, containing 10% Compound B and 2.5% Pluronic F68. 125 ml of slurry was added to a 500 ml Pyrex glass bottle containing 250 ml of 0.8 mm Yttria-Doped-Zirconia media and milled on a U.S. Stoneware mill. The milling was performed at room temperature. Formulation M was milled for 48 hours. Formulation L was prepared by autoclaving Formulation M at 126° C. for 3 min.

Each of the three formulations was then autoclaved, followed by particle size analysis with a Horiba LA-910 particle sizer.

Surprisingly, the results showed that the ending size of the S formulation, having a starting mean particle size of about 110 nm, was the largest among the three tested samples. The S formulation was also the only formulation that had a bimodal size distribution following autoclaving. In contrast, the final particle size of the autoclaved M and L formulations was smaller than the final particle size of the S formulation, and unimodal in size distribution.

A unimodal particle size distribution is preferred, because a composition having widely variable particle sizes (such as in a bimodal particle size distribution) will have inconsistent absorption and consequently bioavailability. Moreover, such compositions are difficult to formulate into dosages providing consistent quantities of drug.

EXAMPLE 3

The purpose of this example was to compare the effect on particle size of autoclaving nanoparticulate compositions of Compound B having starting mean particle sizes of about 108 nm and about 216 nm.

Three different nanoparticulate formulations of Compound B and Pluronic F68™ were made. Formulations I and II had mean particle sizes of 227 and 224 nm, respectively, and Formulation III had a mean particle size of 108 nm.

Formulations I and II were prepared by adding about 600 grams of 4% Pluronic F68™ solution and about 100 grams of Compound B to a 2 L Pyrex glass bottle containing 4 kilograms of 0.8 mm Yttria-Doped-Zirconia media. The mixture was roller milled at room temperature for 72 hours on a U.S. Stoneware roller mill.

Formulation III was prepared using a two step milling process. For the first step, about 700 grams of 9% Pluronic F68™ solution and about 130 grams of Compound B were mixed to form a slurry. Next, 800 grams of slurry was loaded in a 1000 ml vessel and milled in a circulation mode, with 500 μm polymeric media in a 300 ml chamber, in a Dyno Mill (Glen Mills Inc., Clifton, N.J.), for 14 hours. The second milling step was done in a batch mode, wherein 85 grams of dispersion from the first milling step was processed with 50 μm polymeric media in a 150 ml chamber for 6 hours.

Formulations I and II were prepared by adding water-for-injection (WFI) (described in *Pharmaceutical Engineering*, 11:15–23 (1991)) or surface stabilizer powder (i.e., Pluronic F68™ powder) to adjust the final concentration and drug to surface stabilizer ratio. Formulations I and II had a drug to surfactant ratio of 2:1.2 and 2:1, respectively. Formulation III was prepared by adding WFI to dilute the samples 30 fold. All testing formulations were vortexed extensively to ensure the solubilization of Plurionic F68™ powder.

For Formulations I and II, one mL of formulation was added to a 10 ml glass crimp top vial and sealed before autoclaving for 25 min. at 121° C. Three samples of each Formulation were autoclaved (for Formulation I, Sample ##1, 2, and 3, and for Formulation II, Sample ##4, 5, and 6). For Formulation III, five ml of formulation was added to four 20 ml crimp top vials and sealed. Two vials were autoclaved for 10 min. at 121° C. (Samples ##7 and 8) and two vials were autoclaved for 20 min. at 121° C. (Sample ##9 and 10).

Following autoclaving, the particle size distribution of each sample was analyzed with a Horiba LA-910 particle sizer. The results are shown below in Table II.

TABLE II

| Sample | Mean Particle Size | 90% tile Particle Size | Standard Deviation |
| --- | --- | --- | --- |
| 204 nm standard | 213 nm | 251 nm | 28 nm |
| Formulation I | 227 nm | 319 nm | 90 nm |
| Autoclaved Sample #1 | 377 nm | 638 nm | 205 nm |
| Autoclaved Sample #2 | 379 nm | 637 nm | 203 nm |
| Autoclaved Sample #3 | 381 nm | 644 nm | 213 nm |
| Formulation II | 224 nm | 314 nm | 88 nm |
| Autoclaved Sample #4 | 395 nm | 692 nm | 249 nm |
| Autoclaved Sample #5 | 388 nm | 671 nm | 233 nm |
| Autoclaved Sample #6 | 390 nm | 676 nm | 234 nm |
| Formulation III | 108 nm | 160 nm | 47 nm |
| Autoclaved Sample #7 | 649 nm | 1260 nm | 430 nm |
| Autoclaved Sample #8 | 653 nm | 1256 nm | 425 nm |
| Autoclaved Sample #9 | 778 nm | 1498 nm | 530 nm |
| Autoclaved Sample #10 | 758 nm | 1444 nm | 495 nm |

The results show that the nanoparticulate compositions having a mean particle size of about 220 nm (Formulations I and II) showed modest growth following heat sterilization, with the compositions having a mean particle size of under 400 nm, with 90% of the particles having a size less than about 650 or 700 nm. In contrast, the nanoparticulate compositions having a mean particle size of about 108 nm (Formulation III) showed dramatic growth following heat sterilization, with the compositions having a mean particle size of about 650 to about 780 nm, almost twice that of Formulations I and II. In addition, 90% of the particles of Formulation III had a particle size of less than about 1250 to about 1500 nm, which is more than double that of Formulations I and II.

Microscopic pictures confirm the particle size reading by the Horiba sizer. No aggregation or chunks were observed under microscope in any of the Formulation I and II autoclaved samples.

Doublets were observed in the chromatograms of the four samples of Formulation III (having a mean starting particle size of 108 nm), but not in the samples of Formulation I or II (having mean starting particle sizes of 227 and 224 nm, respectively). A doublet indicates that the formulation has a wide particle size distribution, which is undesirable for pharmaceutical formulations.

The results suggest that a smaller mean starting particle size does not result in an autoclaved formulation having a small mean particle size. Rather, there is an optimum particle size which enables nanoparticulate compositions to be autoclaved without significant particle aggregation.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

What is claimed is:

1. A nanoparticutate formulation that exhibits minimal particle aggregation or crystal growth following exposure to elevated temperatures, wherein the composition comprises:
   (a) a water-insoluble crystalline drug; and
   (b) one or more surface stabilizers adsorbed to the surface of the drug, wherein at least 50% of the drug particles in the composition have a weight average particle size of from about 150 nm to about 350 nm,
       wherein the nanoparticulate composition has been exposed to elevated temperatures for heat sterilization.

2. The composition of claim 1, wherein the drug is present in an amount of about 99.9 to about 10% (w/w).

3. The composition of claim 2, wherein the one or more surface stabilizers are present in an amount of about 0.1 to about 90% (w/w).

4. The composition of claim 1, wherein the drug is selected from the group consisting of a crystalline phase drug and an amorphous phase drug.

5. The composition of claim 1 having an effective average particle size selected from the group consisting of from about 150 nm to about 300 nm, from about 150 mn to about 250 nm, and from about 150 nm to about 200 nm.

6. The composition of claim 1 in an injectable formulation.

7. The composition of claim 1, wherein at least one of the one or more surface stabilizers is a polyoxyethylene sorbitan fatty acid ester.

8. The composition of claim 1, wherein at least one of the one or more surface stabilizers is a detergent.

9. The composition of claim 1, wherein the composition exhibits minimal particle aggregation or crystal growth following a storage period of 1 month or more or following exposure to elevated temperatures.

10. The composition of claim 1, wherein the composition exhibits minimal particle aggregation or crystal growth following a storage period of 4 months or more or following exposure to elevated temperatures.

11. The composition of claim 1, wherein the composition exhibits minimal particle aggregation or crystal growth following a storage period of 7 months or more or following exposure to elevated temperatures.

12. The composition according to claim 1, wherein at least 70% of drug particles in the composition have a weight average particle size of from about 150 nm to about 350 nm.

13. The composition according to claim 1, wherein at least 90% of drug particles in the composition have a weight average particle size of from about 150 nm to about 350 nm.

14. The composition according to claim 1, wherein at least 95% of drug particles in the composition have a weight average particle size of from about 150 nm to about 350 nm.

15. A method for preventing crystal growth and particle aggregation in a nanoparticulate composition during heating or storage, said method comprising:
   (a) forming a nanoparticulate composition of a poorly soluble crystalline drug having one or more non-crosslinked surface stabilizers adhered to the surface of the drug, wherein at least 50% of the drug particles in the composition have a weight average particle size of from about 150 nm to about 350 nm; and
   (b) exposing the nanoparticulate composition to elevated temperatures for heat sterilization,
       wherein the nanoparticulate composition exhibits minimal particle size growth and/or aggregation during storage following exposure to the elevated temperatures.

16. The method of claim 15, wherein the nanoparticulate composition is formed by grinding the poorly soluble drug in the presence of media.

17. The method of claim 15, further comprising heat autoclaving the nanoparticulate preparation in a sealed autoclavable container.

18. The method of claim 15, wherein the drug is present in an amount of about 99.9 to about 10% (w/w).

19. The method of claim 15, wherein the one or more surface stabilizers are present in an amount of about 0.1 to about 90% (w/w).

20. The method of claim 15, wherein the drug is selected from the group consisting of a crystalline phase drug and an amorphous phase drug.

21. The method of claim 15, wherein the nanoparticulate composition has an effective average particle size selected from the group consisting of from about 150 nm to about 300 nm, from about 150 nm to about 250 nm, and from about 150 nm to about 200 nm.

22. The method of claim 15, wherein at least one of the one or more surface stabilizers is a polyoxyethylene sorbitan fatty acid ester.

23. The method of claim 15, wherein at least one of the one or more surface stabilizers is a detergent.

24. The method according to claim 15, wherein at least 70% of drug particles in said nanoparticulate composition have a weight average particle size of from about 150 nm to about 350 nm.

25. The method according to claim 15, wherein at least 90% of drug particles in said nanoparticulate composition have a weight average particle size of from about 150 nm to about 350 nm.

26. The method according to claim 15, wherein at least 95% of drug particles in said nanoparticulate composition have a weight average particle size of from about 150 nm to about 350 nm.

27. A method of administering a nanoparticulate composition to a mammal in need, wherein the nanoparticulate composition exhibits minimal particle size or crystal growth following exposure to elevated temperatures, and wherein the composition comprises:

(a) a water-insoluble crystalline drug; and (b) one or more surface stabilizers adsorbed to the surface of the drug, wherein at least 50% of the drug particles in the composition have a weight average particle size of from about 150 nm to about 350 nm said method comprising administering to a mammal in need a therapeutically effective amount of the nanoparticulate composition.

28. The method of claim 27, wherein the nanoparticulate composition has an effective average particle size selected from the group consisting of from about 150 nm to about 300 nm, from about 150 nm to about 250 nm, and from about 150 nm to about 200 nm.

29. The method according to claim 27, wherein at least 70% of drug particles in said nanoparticulate composition have a weight average particle size of from about 150 nm to about 350 nm.

30. The method according to claim 27, wherein at least 90% of drug particles in said nanoparticulate composition have a weight average particle size of from about 150 nm to about 350 nm.

31. The method according to claim 27, wherein at least 95% of drug particles in said nanoparticulate composition have a weight average particle size of from about 150 nm to about 350 nm.

* * * * *

UNITED STATES PATENT AND TRADEMARK OFFICE
CERTIFICATE OF CORRECTION

PATENT NO. : 6,267,989 B1  
APPLICATION NO. : 09/263834  
DATED : July 31, 2001  
INVENTOR(S) : Liversidge et al.

Page 1 of 1

It is certified that error appears in the above-identified patent and that said Letters Patent is hereby corrected as shown below:

Title page item (73) Assignee:

Please change "Klan Pharma International Ltd.", to -- Elan Pharma International Ltd. --

Signed and Sealed this

Eighth Day of September, 2009

David J. Kappos
*Director of the United States Patent and Trademark Office*